(12) United States Patent
Lannibois-Drean et al.

(10) Patent No.: US 7,288,575 B2
(45) Date of Patent: Oct. 30, 2007

(54) PROCESS FOR PREPARING AN EMULSION WHOSE ORGANIC PHASE IS OF HIGH VISCOSITY

(75) Inventors: Hélène Lannibois-Drean, Charenton le Pont (FR); Mikel Morvan, Princeton, NJ (US); Marie-Pierre Labeau, Paris (FR); Christine Vidil, Communay (FR)

(73) Assignee: Rhodia Chimie (FR)

( * ) Notice: Subject to any disclaimer, the term of this patent is extended or adjusted under 35 U.S.C. 154(b) by 0 days.

(21) Appl. No.: 11/145,737

(22) Filed: Jun. 6, 2005

(65) Prior Publication Data

US 2005/0228126 A1    Oct. 13, 2005

Related U.S. Application Data

(63) Continuation of application No. 10/399,483, filed on Oct. 17, 2003, now abandoned.

(51) Int. Cl.
*B01F 3/08* (2006.01)
*B01F 17/52* (2006.01)
*C08J 3/07* (2006.01)
*C08L 51/00* (2006.01)

(52) U.S. Cl. .................. 516/53; 524/543; 524/800

(58) Field of Classification Search ............... 516/53; 524/543, 800
See application file for complete search history.

(56) References Cited

U.S. PATENT DOCUMENTS 6,288,137 B1 *  9/2001  Iliopoulos et al. .......... 523/105

FOREIGN PATENT DOCUMENTS

EP              629649 A1 * 12/1994

* cited by examiner

*Primary Examiner*—Kelechi C. Egwim
(74) *Attorney, Agent, or Firm*—Hunton & Williams LLP

(57) ABSTRACT

The invention concerns a method for preparing an oil-in-water emulsion whereof the organic phase has a viscosity not less than 1 Pa.s, which consists in using an aqueous phase comprising at least a heat-thickening polymer having a viscosity jump between 25 and 80° C. so that the value of the ratio log 10 (viscosity at 80° C.)/log 10 (viscosity at 25° C.) is at least equal to 1, preferably at least equal to 2, the variation in viscosity being reversible; the amount of heat-thickening polymer being such that the aqueous phase viscosity is 0.2 to 5 times that of the organic phase at the temperature for preparing the emulsion; the latter being not less than the thickening temperature of the heat-thickening polymer.

21 Claims, No Drawings

PROCESS FOR PREPARING AN EMULSION WHOSE ORGANIC PHASE IS OF HIGH VISCOSITY

This application is a continuation of U.S. application Ser. No. 10/399,483, filed on Oct. 17, 2003 now abandoned.

The present invention relates to a process for preparing an emulsion whose organic phase is of high viscosity.

Difficulties are encountered in preparing emulsions with a relatively small droplet size, and obtained from an aqueous continuous phase and an organic discontinuous phase of high viscosity, i.e. with a viscosity at least equal to 1 Pa.s and preferably at least 5 Pa.s. Specifically, the difference in viscosity between the continuous and discontinuous phases is such that it is necessary to use high-shear and/or low-efficiency means. In addition, the results achieved are only partially satisfactory.

Solutions have been proposed for obtaining oil-in-water emulsions via standard means. These emulsions are obtained in particular by using large amounts of surfactants. Thus, the process is performed starting with a concentrated aqueous solution of surfactant, as base stock, to which is added the organic phase. The emulsion obtained may then be diluted.

The drawback of this process is that it requires the use of specially designed equipment. Furthermore, this type of process cannot be carried out continuously.

In addition, it is not possible to prepare multiple emulsions (water-in-oil-in-water) using the process described above. The reason for this is that as soon as the inverse emulsion (water-in-oil) is introduced into the concentrated aqueous phase of surfactants, the inverse emulsion is destabilized and only a simple emulsion (oil-in-water) may be obtained.

The object of the present invention is to obtain a simple and efficient process for preparing an oil-in-water emulsion from a viscous organic phase, i.e., firstly, requiring the use of only standard means, and, secondly, making it possible to obtain a fine and uniform particle size for the emulsion.

Furthermore, the present invention is most particularly suitable for obtaining multiple emulsions.

Thus, one subject of the present invention is a process for preparing an oil-in-water emulsion, the organic phase of which has a viscosity of greater than or equal to 1 Pa.s, in which an aqueous phase is used comprising at least one heat-induced thickening polymer displaying a jump in viscosity between 25 and 80° C. such that the value of the ratio $\log_{10}$ (viscosity at 80° C.)/$\log_{10}$ (viscosity at 25° C.) is at least equal to 1 and preferably at least equal to 2, the variation in viscosity being reversible; the amount of heat-induced thickening polymer being such that the viscosity of the aqueous phase is from 0.2 to 5 times that of the organic phase at the emulsion preparation temperature; said temperature being greater than or equal to the thickening temperature of the heat-induced thickening polymer.

However, other characteristics and advantages of the present invention will emerge more clearly on reading the description and the example that follow.

Firstly, it should be noted that the process according to the invention may be carried out to obtain simple oil-in-water emulsions, but also for multiple emulsions for which the organic phase is in fact an inverse emulsion (i.e. water-in-oil emulsion).

It is pointed out that the mean droplet size of a simple emulsion obtained according to the invention is more particularly between 0.1 and 50 µm and preferably between 0.1 and 5 µm.

In the case of multiple emulsions obtained according to the invention, the mean size of the droplets dispersed in the external aqueous phase is between 5 and 100 µm, more particularly between 5 and 50 µm and advantageously between 5 and 15 µm.

The mean droplet sizes are measured using a Horiba granulometer, and correspond to the median volume diameter (d50) which represents the diameter of the particle equal to 50% of the cumulative distribution.

In the text hereinbelow, the term "emulsion" is used either to denote a simple direct emulsion (oil-in-water), an inverse emulsion (water-in-oil) or a multiple emulsion, unless the nature of the emulsion is specifically indicated.

In the text hereinbelow, reference will be made to the "internal aqueous phase" to denote the aqueous phase of the inverse emulsion of the multiple emulsion. The term "aqueous phase" will denote either the aqueous phase of a simple direct emulsion, or the "external" aqueous phase of a multiple emulsion.

Moreover, the term "polymers" denotes both homopolymers and copolymers.

The organic phase will now be described.

Firstly, the compound used as organic phase is chosen more particularly from compounds whose solubility in water does not exceed 10% by weight at 25° C.

In addition, as has been indicated previously, the organic phase has a viscosity of at least 1 Pa.s and preferably of at least 5 Pa.s. The process according to the invention is most particularly suitable for preparing emulsions for which the organic phase has a viscosity of between 5 and 500 Pa.s.

It should be noted that the viscosity refers to the dynamic viscosity, measured at 25° C. using a Brookfield viscometer according to AFNOR standard NFT 76 102 of February 1972.

The organic phase is more particularly chosen from mineral oils; alkyd resins (such as, for example, the Coporob 3115 DE resins sold by the company Novance); polyisocyanates; high molecular weight silicones; these compounds being alone or as a mixture.

Among the mineral oils that may be mentioned are polybutene oils. For example, the polybutene oils obtained by polymerization of the C fraction, the isobutene proportion of which is high (Napvis and Hyvis ranges from BP), are suitable for use.

As regards the polyisocyanates, mention may be made especially of the compounds having the following formula: $A(\text{—NCOblock})_p$, in which A represents an organic skeleton containing n free valences, p being between 2 and 7, and NCOblock represents a masked or unmasked isocyanate function.

More particularly, the total number of carbons in said monomer is advantageously between 10 and 100.

In addition, the A skeleton may be made up of a heavy polyamine, including anilines, for example with a carbon number at least equal to 6, more particularly at least equal to 10, preferably at least equal to 15. This amine is converted in a manner that is known per se by reaction with phosgene. It should be noted that the A skeleton may also be that of trimers and biurets.

Among the masking groups that may be chosen are groups containing labile hydrogen, with a pKa value of not more than 14, more particularly not more than 10 and preferably not more than 8. It should be noted that, the higher the pKa value, the more desirable it is for the masking agent, if present, to be volatile.

The masking agents are chosen such that the emulsion is stable at its storage temperature.

Among the chemical functions capable of masking isocyanates, examples that may be mentioned are the following functions:

alcohols and thiols
oximes
hydroxylamines
acids
amides and imides
β-diketones
pyrazoles.

The polyisocyanates that are suitable are more particularly chosen from oils and/or gums and/or resins containing (poly)isocyanate groups, the viscosity of which is within ranges indicated previously. It would not constitute a departure from the context of the invention to use several compounds of this type, and likewise their combination with at least one solvent (or diluent) for said oil and/or gum and/or resin, provided that the viscosity of the whole is within the range indicated.

Among the high molecular weight silicones that may be mentioned, for example, are polyorgano-siloxane oils and/or gums and/or resins. It would not constitute a departure from the context of the present invention to use mixtures of polyorganosiloxane oil(s) and/or gum(s) and/or resin(s), provided that the mixtures have a viscosity within the ranges indicated previously. Similarly, the invention is suitable for emulsifying mixtures of polyorganosiloxane oil(s) and/or gum(s) and/or resin(s), and optionally of at least one solvent for said oil(s) and/or gum(s) and/or resin(s), and/or optionally of at least one silane and/or of at least one siliceous and/or nonsiliceous filler, provided that the mixtures have viscosities within the mentioned range.

Among the polyorganosiloxane oils and gums that may be used, mention may be made of those consisting of units of formulae

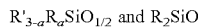

$R'_{3-a}R_aSiO_{1/2}$ and $R_2SiO$ in which formulae:
a is an integer from 0 to 3
the radicals R, which may be identical or different, represent a saturated or unsaturated $C_1$-$C_{10}$ aliphatic radical; a $C_6$-$C_{13}$ aromatic radical; a polar organic group linked to the silicon via an Si—C or Si—O—C bond; a hydrogen atom;
the radicals R', which may be identical or different, represent an OH group; a $C_1$-$C_{10}$ alkoxy or alkenyloxy radical; a $C_6$-$C_{13}$ aryloxy radical; a $C_1$-$C_{13}$ acyloxy radical; a $C_1$-$C_8$ ketiminoxy radical; a $C_1$-$C_6$ amino-functional or amido-functional radical, linked to the silicon via an Si—N bond.

Preferably, at least 80% of the radicals R of said oils represent a methyl group.

Among the polyorganosiloxane resins that may be used, mention may be made of those consisting of units of formulae:

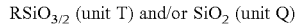

$RSiO_{3/2}$ (unit T) and/or $SiO_2$ (unit Q)

combined with units of formulae:

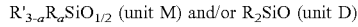

$R'_{3-a}R_aSiO_{1/2}$ (unit M) and/or $R_2SiO$ (unit D)

in which formulae a, R and R' have the definition given above.

These resins are generally of the type MQ, MDQ, TDM, TD, MT, etc.

When said oils, gums or resins contain reactive and/or polar radicals R, such as H, OH, vinyl, allyl, hexenyl or aminoalkyl, especially, these radicals generally represent not more than 2% of the weight of the oil or gum and not more than 10% of the weight of the resin.

The viscous polydimethylsiloxane and α,ω-bis-(hydroxy) polydimethylsiloxane oils and the poly-dimethylsiloxane, polyphenylmethylsiloxane and α,ω-bis-(hydroxy)polydimethylsiloxane gums are well-known commercially available products.

The DT polymethylsiloxane viscous resins containing from 1% to 2% by weight of silanol functions are also commercially available products.

Among the solvents for the silicone oils, gums or resins, which may be present in the silicone phase, mention may be made of volatile cyclic organo-polysiloxanes (octamethylcyclotetrasiloxane, deca-methylcyclopentasiloxane, etc.), short-chain poly-dimethylsiloxane oils (viscosity of less than 100 mPa.s), hexamethyldisiloxane, ketones (methyl ethyl ketone, etc.), ethers (diethyl ether, etc.), esters (isopropyl myristate, ethyl acetate, etc.), certain chlorinated or chlorofluorinated solvents (methylene chloride, chloroform, etc.), and highly branched paraffins (white oils based on isoalkanes and cycloalkanes, etc.).

Various silanes and/or mineral fillers may also be present in the silicone phase.

These silanes may especially be synthetic byproducts or crosslinking agents for said polyorgano-siloxane oils, gums or resins. They are generally present in amounts of from about 0 to 10 parts by weight, preferably of from about 0 to 5 parts by weight per 100 parts by weight of polyorganosiloxane oil(s) and/or gum(s) and/or resin when they are reaction byproducts.

When the crosslinking-agent function of the hydroxylated oils, gums or resins is desired, they are generally present in amounts from about 0.5 to 30 parts by weight, and preferably from about 2 to 8 parts by weight per 100 parts by weight of oil(s) and/or gum(s) and/or resin(s).

Said silanes may also be an additive for modulating the physicochemical properties and especially the adhesion properties of the silicone compositions of various applications obtained from the aqueous emulsions prepared according to the process of the invention. Among this category of silanes that may be mentioned are aminopropyltriethoxysilane, amino-propylmethyldiethoxysilane, glycidoxypropyltrimethoxy-silane, etc.

They are used in amounts that may be up to 200%, generally from about 2% to 100%, of the weight of oil(s) and/or gum(s) and/or resin(s).

Reinforcing or semi-reinforcing siliceous or nonsiliceous fillers may also be present. Examples that may be mentioned include colloidal silicas, combustion silica and precipitation silica powders, diatomaceous earths, ground quartz, natural calcium carbonate, hydrated alumina, magnesium hydroxide, carbon black, titanium dioxide, aluminum oxide, vermiculite, zinc oxide, mica, talc, iron oxide, barium sulfate, slaked lime, etc.

The size of these fillers is generally less than or equal to the mean size of the droplets in which they are dispersed. As a guide, the mean size of these fillers ($d_{50}$) is generally from about 0.001 to 50 μm and preferably from about 0.001 to 10 μm.

The fillers are generally present in amounts that may be up to 300% and preferably from about 3% to 100% of the weight of oil(s) and/or gum(s) and/or resin(s).

The organic phase may likewise be chosen from epoxy resins, essential oils, mono-, di- and triglycerides, provided that their viscosity is within the range mentioned previously.

The organic phase may optionally comprise at least one hydrophobic active material.

It should be noted that the organic phase itself may constitute the hydrophobic active material provided that the organic phase has a dynamic viscosity within the range mentioned previously.

In the case where it is different than the organic phase, the active material is in liquid or nonliquid form, soluble in the organic phase or dissolved in an organic solvent that is miscible with said organic phase, or alternatively in the form of a solid dispersed in said phase.

More particularly, the active materials are such that their solubility in water does not exceed 10% by weight, at 25° C.

In addition, the active materials preferably have a melting point of less than or equal to 100° C. and more particularly less than or equal to 80° C.

As examples of materials that are active in the food sector, mention may be made of mono-, di- and triglycerides, essential oils, flavorings and colorants.

As examples of materials that are active in cosmetics, mention may be made of silicone oils belonging, for example, to the dimethicone family; lipophilic vitamins, for instance vitamin A.

As examples of active materials that are suitable for performing the invention, in the field of paints, mention may be made of alkyd resins, epoxy resins and masked or unmasked isocyanates.

In the paper sector, examples that may be mentioned include sizing resins and water-repellant resins such as alkylketene dimer (AKD) or alkenyl-succinic anhydride (ASA).

In the agrochemicals sector, the plant-protection active materials may be chosen from the family of α-cyano-phenoxybenzyl carboxylates or α-cyano-halophenoxy carboxylates, the family of N-methylcarbonates comprising aromatic substituents, active materials such as Aldrin, Azinphos-methyl, Benfluralin, Bifenthrin, Chlorphoxim, Chlorpyrifos, Fluchloralin, Fluroxypyr, Dichlorvos, Malathion, Molinate, Parathion, Permethrin, Profenofos, Propiconazole, Prothiofos, Pyrifenox, Butachlor, Metolachlor, Chlorimephos, Diazinon, Fluazifop-P-butyl, Heptopargil, Mecarbam, Propargite, Prosulfocarb, Bromophos-ethyl, Carbophenothion or Cyhalothrin.

In the detergency sector, possible active materials that may be mentioned are silicone antifoams.

It is similarly possible to use active materials such as those forming part of the composition of lubricants for working or deforming materials. The active material is usually an oil, an oil derivative or a fatty acid ester or a fatty acid salt.

The active material may also be chosen from organic solvents or mixtures of such solvents that are sparingly miscible or immiscible in water, especially such as those used for cleaning or stripping, such as aromatic petroleum fractions, terpenic compounds, for instance D- or L-limonenes, and also solvents such as Solvesso®. Solvents that are also suitable include aliphatic esters, for instance the methyl esters of a mixture of acetic acid, succinic acid and glutaric acid (acid mixture obtained as a byproduct of Nylon synthesis), oils, for instance liquid petroleum jelly, and chlorinated solvents.

In the case where the organic phase comprises one or more hydrophobic active materials different than the organic phase, their content more particularly represents 1% to 50% by weight of said organic phase.

According to one variant of the present invention, the organic phase comprises a dispersed internal aqueous phase. More particularly, the organic phase is an inverse emulsion.

It should be noted that the viscosity of the inverse emulsion, i.e. of the organic phase comprising the internal aqueous phase, itself also has a high viscosity. Thus, the viscosity of the inverse emulsion is at least 1 Pa.s, more particularly at least 5 Pa.s and preferably between 5 and 500 Pa.s. The viscosities mentioned above are dynamic viscosities measured using a Brookfield viscometer at 25° C., according to standard NFT 76 102 of February 1972.

In such a case, the organic phase of the inverse emulsion is preferably of the same nature as that of a simple emulsion. Reference may thus be made at any point to the list given above.

The internal aqueous phase, if present, and/or the external aqueous phase of the emulsion may comprise at least one hydrophilic active material. Preferably, the hydrophilic active material is in the internal aqueous phase of the emulsion, when it is present.

It is pointed out that the hydrophobic and hydrophilic active materials are determined as a function of their mutual compatibility. Similarly, the hydrophilic active material is chosen so as not to interfere with the organic phase.

The hydrophilic active material may be in a form that is soluble in the aqueous phase; in a form dissolved in a water-miscible solvent, for instance methanol, ethanol, propylene glycol or glycerol, for example; or in the form of a solid dispersed in said phase.

As examples of active materials that may be used in the cosmetics field, mention may be made of substances that have a cosmetic effect, a therapeutic effect or any other substance that may be used for treating the skin and the hair.

Thus, active materials that may be used include skin and hair conditioners such as, especially, polymers comprising quaternary ammoniums, which may optionally be incorporated in heterocycles (compounds of the quaternium, polyquaternium, etc. type), humectants; fixing (styling) agents more particularly chosen from polymers (homo-, co- or terpolymers, for example acrylamide, acrylamide/sodium acrylate, polystyrene sulfonate, etc.), cationic polymers, polyvinylpyrrolidone, polyvinyl acetate, etc.

It is similarly possible to use colorants; astringents, which may be used in deodorants and which are more particularly aluminum or zirconium salts; antibacterial agents; antiinflammatory agents, anesthetics, sunscreens, etc.

Mention may also be made of α- and β-hydroxy acids, for instance citric acid, lactic acid, glycolic acid and salicylic acid; dicarboxylic acids, preferably unsaturated and containing 9 to 16 carbon atoms, for instance azelaic acid; vitamin C and its derivatives, especially the glycosylated and phosphated derivatives; biocides, especially cationic biocides (especially Glokill PQ and Rhodaquat RP50, sold by Rhodia Chimie).

In the food sector, examples that may be mentioned include divalent calcium salts (phosphates, chlorides, etc.) used as crosslinking agent for texturing polymers, for instance alginates and carrageenans; sodium bicarbonate, inter alia.

In the field of plant-protection active materials, hydrophilic pesticides or hydrophilic nutrient elements that promote the growth and development of plants may be used.

As regards the field of exploitation or construction of oil or gas wells, the present invention may be carried out for hydrophilic active materials that may be used especially during operations of cementation, completion, drilling and stimulation of wells (for example fracturing). As examples of active materials that may be used in this field, mention may be made of crosslinking catalysts for cement compositions such as, for example, lithium salts, for instance the chloride or the acetate. Mention may similarly be made of compounds that are capable, inter alia, of degrading polysaccharides, such as, for example, carboxylic acids (especially citric acid), enzymes (especially cellulases) and oxidizing agents.

In the field of silicones, examples that may be mentioned include the calcium salts and potassium hydroxide, which are used as crosslinking agent.

In the field of papermaking, mention may be made especially of calcium chloride and hydrochloric acid.

The amount of hydrophilic active material is more particularly between 0.1% and 50% by weight relative to the aqueous phase (whether it is internal and/or external) and preferably between 0.1% and 20% by weight relative to the aqueous phase (internal and/or external).

When an internal aqueous phase is present, the internal aqueous phase/organic phase weight ratio is more particularly between 10/90 and 90/10. This weight ratio is preferably between 30/70 and 80/20.

Still according to this variant, i.e. according to the one in which the organic phase is in the form of an inverse emulsion, the inverse emulsion also comprises at least one nonionic surfactant and/or at least one amphiphilic block polymer and/or at least one cationic surfactant.

According to a first variant, the inverse emulsion comprises at least one nonionic surfactant or at least one amphiphilic block polymer, or a blend of the two.

It should be noted that the Bancroft rule may be applied to the nonionic surfactant and to the amphiphilic block polymer used ($2^{\text{ème}}$ Congrés Mondial de l'Emulsion [2nd World Conference on Emulsions], 1997, Bordeaux, France). In other words, the fraction soluble in the continuous phase is greater than the fraction soluble in the disperse phase.

Thus, the surfactant and the polymer are preferably chosen from those that satisfy both the conditions below:
  when they are mixed with the internal organic phase, at a concentration of between 0.1% and 10% by weight of said phase at 25° C., they are in the form of a solution throughout all or part of the indicated concentration range;
  when they are mixed with the internal aqueous phase, at a concentration of between 0.1% and 10% by weight of said phase and at 25° C., they are in the form of a dispersion throughout all or some of the indicated concentration range.

More particularly, the nonionic surfactant is chosen from compounds with an HLB (hydrophilic/lipophilic balance) value of less than or equal to 8.

As examples of surfactants that may form part of the composition of the inverse emulsion, mention may be made of surfactants, alone or as a mixture, chosen from:
  alkoxylated fatty alcohols
  alkoxylated triglycerides
  alkoxylated fatty acids
  optionally alkoxylated sorbitan esters
  alkoxylated fatty amines
  alkoxylated di(1-phenylethyl)phenols
  alkoxylated tri(1-phenylethyl)phenols
  alkoxylated alkylphenols the number of alkoxylated (ethoxylated, propoxylated or butoxylated) units is such that the HLB value is less than or equal to 8.

The alkoxylated fatty alcohols generally contain from 6 to 22 carbon atoms, the alkoxylated units being excluded from these numbers.

The alkoxylated triglycerides may be triglycerides of plant or animal origin.

The optionally alkoxylated sorbitan esters are esters of cyclized sorbitol of fatty acid containing from 10 to 20 carbon atoms, for instance lauric acid, stearic acid or oleic acid.

The alkoxylated fatty amines generally contain from 10 to 22 carbon atoms, the alkoxylated units being excluded from these numbers.

The alkoxylated alkylphenols generally contain one or two linear or branched alkyl groups containing 4 to 12 carbon atoms. Examples that may especially be mentioned include octyl, nonyl and dodecyl groups.

As regards the amphiphilic block polymer, it comprises at least two blocks.

These amphiphilic polymers, which satisfy the Bancroft rule and the two conditions stated previously, more particularly comprise at least one hydrophobic block and at least one neutral, anionic or cationic hydrophilic block.

In the case where the amphiphilic polymer comprises at least three blocks, and more particularly three blocks, the polymer is preferably linear: in addition, the hydrophobic blocks are more particularly located at the ends.

In the case where the polymers comprise more than three blocks, these polymers are preferably in the form of grafted or comb polymers.

In the text hereinbelow, even though this is an abuse of language, the term "amphiphilic block polymer" will be used either for the linear block polymers or for the grafted or comb polymers.

Said amphiphilic polymers may advantageously be obtained by "living" or controlled free-radical polymerization. As nonlimiting examples of living or controlled polymerization processes, reference may be made especially to patent applications WO 98/58974 (xanthate), WO 97/01478 (dithioesters), WO 99/03894 (nitroxides); WO 99/31144 (dithiocarbamates).

The amphiphilic polymers may also be obtained by cationic or anionic polymerization.

They may similarly be prepared by using ring-opening polymerizations (especially anionic or cationic polymerizations), or by chemical modification of the polymer.

The grafted or comb polymers may also be obtained by "direct grafting" and copolymerization methods.

Direct grafting consists in polymerizing the chosen monomer(s) via a free-radical route, in the presence of the selected polymer to form the skeleton of the final product. If the monomer/skeleton couple and the operating conditions are carefully chosen, there may then be a transfer reaction between the growing macroradical and the skeleton. This reaction generates a radical on the skeleton and it is from this radical that the graft grows. The primary radical derived from the initiator may also contribute to the transfer reactions.

As regards copolymerization, this involves in a first stage the grafting, onto the end of the future pendent segment, of a free-radical-polymerizable function. This grafting may be performed by usual methods of organic chemistry. Next, in a second stage, the macromonomer thus obtained is polymerized with the chosen monomer to form the skeleton, and a "comb" polymer is obtained.

Among the hydrophobic monomers from which the hydrophobic block(s) of the amphiphilic polymer may be prepared, mention may be made especially of:

linear, branched, cyclic or aromatic monocarboxylic or polycarboxylic acid esters, comprising at least one ethylenic unsaturation, saturated carboxylic acid esters containing 8 to 30 carbon atoms, optionally bearing a hydroxyl group;

α,β-ethylenically unsaturated nitriles, vinyl ethers, vinyl esters, vinylaromatic monomers, and vinyl or vinylidene halides, linear or branched, aromatic or nonaromatic hydrocarbon-based monomers, comprising at least one ethylenic unsaturation, monomers of cyclic or noncyclic siloxane type, and chlorosilanes;

propylene oxide or butylene oxide; alone or as mixtures, and also the macromonomers derived from such monomers.

As particular examples of hydrophobic monomers that may be included in the preparation of the hydrophobic block(s) of the amphiphilic block polymer, mention may be made of:

esters of (meth)acrylic acid with an alcohol containing 1 to 12 carbon atoms, for instance methyl (meth)acrylate, ethyl (meth)acrylate, propyl (meth)acrylate, n-butyl (meth)acrylate, t-butyl (meth)acrylate, isobutyl (meth)acrylate or 2-ethyl-hexyl acrylate;

vinyl acetate, vinyl Versatate®, vinyl propionate, vinyl chloride, vinylidene chloride, methyl vinyl ether or ethyl vinyl ether;

vinyl nitrites more particularly including those containing from 3 to 12 carbon atoms such as, in particular, acrylonitrile and methacrylonitrile;

styrene, α-methylstyrene, vinyltoluene, butadiene and chloroprene;

alone or as mixtures, and also macromonomers derived from such monomers.

The preferred monomers are esters of acrylic acid with linear or branched $C_1$-$C_4$ alcohols, such as methyl, ethyl, propyl or butyl acrylate, vinyl esters, for instance vinyl acetate, styrene and α-methyl-styrene.

As regards the nonionic hydrophilic monomers from which the amphiphilic block polymers may be obtained, mention may be made, without wishing to be limited thereto, of ethylene oxide, linear, branched, cyclic or aromatic monocarboxylic or polycarboxylic acid amides, comprising at least one ethylenic unsaturation or derivatives, for instance (meth)acrylamide or N-methylol(meth)acrylamide; hydrophilic esters derived from (meth)acrylic acid, such as, for example, 2-hydroxyethyl (meth)acrylate; vinyl esters allowing the production of polyvinyl alcohol blocks after hydrolysis, for instance vinyl acetate, vinyl Versatate® or vinyl propionate, alone or in combination, and also macromonomers derived from such monomers. It is recalled that the term "macro-monomer" denotes a macromolecule bearing one or more polymerizable functions.

However, the preferred hydrophilic monomers are acrylamide and methacrylamide, alone or as a mixture, or in the form of macromonomers.

As regards the anionic hydrophilic monomers from which the amphiphilic block polymers may be obtained, mention may be made, for example, of monomers comprising at least one carboxylic, sulfonic, sulfuric, phosphonic, phosphoric or sulfosuccinic function, or the corresponding salts.

It is pointed out that, under the pH conditions for the use of the amphiphilic block polymer, the functions of the anionic block(s) of the polymer are in an at least partially ionized (dissociated) form. More particularly, at least 10 mol % of the functions of the block(s) are in ionized form. The determination of this value does not pose any problem to a person skilled in the art; it depends especially on the pKa of the ionizable functions of the units of the polymer and on the number of these functions (i.e. the number of moles of monomer bearing ionizable functions used during the preparation of the polymer).

More particularly, the monomers are chosen from:

linear, branched, cyclic or aromatic monocarboxylic or polycarboxylic acids, and N-substituted derivatives of such acids; polycarboxylic acid monoesters, comprising at least one ethylenic unsaturation;

linear, branched, cyclic or aromatic vinylcarboxylic acids;

amino acids comprising one or more ethylenic unsaturations;

alone or as mixtures, precursors thereof, sulfonic or phosphonic derivatives thereof, and also the macro-monomers derived from such monomers; the monomers or macromonomers possibly being in the form of salts.

Examples of anionic monomers that may be mentioned, without wishing to be limited thereto, include:

acrylic acid, methacrylic acid, fumaric acid, itaconic acid, citraconic acid, maleic acid, acryl-amidoglycolic acid, 2-propene-1-sulfonic acid, methallylsulfonic acid, styrenesulfonic acid, α-acrylamidomethylpropanesulfonic acid, 2-sulfo-ethylene methacrylate, sulfopropylacrylic acid, bis-sulfopropylacrylic acid, bis-sulfopropylmethacrylic acid, sulfatoethylmethacrylic acid, hydroxyethyl-methacrylic acid phosphate monoester, and also the alkali metal salts, for instance the sodium or potassium salts, or the ammonium salts;

vinylsulfonic acid, vinylbenzenesulfonic acid, vinylphosphonic acid, vinylidenephosphoric acid and vinylbenzoic acid, and also the alkali metal salts thereof, for instance the sodium or potassium salts, or the ammonium salts thereof;

N-methacryloylalanine or N-acryloylhydroxyglycine; alone or as mixtures, and also the macromonomers derived from such monomers.

It would not constitute a departure from the context of the present invention to use monomers that are precursors of those which have just been mentioned. In other words, these monomers contain units which, once incorporated into the polymer chain, may be converted, especially by means of a chemical treatment such as hydrolysis, to regenerate the above mentioned anionic species. For example, the totally or partially esterified monomers of the abovementioned monomers may be used in order thereafter to be totally or partially hydrolyzed.

As cationic hydrophilic monomers from which the amphiphilic block polymers may be obtained, mention may be made especially of:

aminoalkyl (meth)acrylates and aminoalkyl (meth)acrylamides;

monomers comprising at least one secondary, tertiary or quaternary amine function, or a heterocyclic group containing a nitrogen atom, vinylamine or ethyleneimine;

diallyldialkylammonium salts;

alone or as a mixture, or the corresponding salts, and also the macromonomers derived from such monomers.

Said monomers may have a counterion chosen from halides such as, for example, chlorine, sulfates, hydrosulfates, alkyl sulfates (for example containing 1 to 6 carbon atoms), phosphates, citrates, formates and acetates.

Examples of cationic monomers that are also suitable include, inter alia, the following monomers:

- dimethylaminoethyl (meth)acrylate, dimethylamino-propyl (meth)acrylate, di-tert-butylaminoethyl (meth)acrylate, dimethylaminomethyl(meth)acrylamide and dimethylaminopropyl(meth)acrylamide;
- ethyleneimine, vinylamine, 2-vinylpyridine or 4-vinylpyridine;
- trimethylammoniumethyl (meth)acrylate chloride, trimethylammoniumethyl acrylate methyl sulfate, benzyldimethylammoniumethyl (meth)acrylate chloride, 4-benzoylbenzyldimethylammoniumethyl acrylate chloride, (meth)acrylamidotrimethylammoniumethyl chloride or vinylbenzyltrimethylammonium chloride;
- diallyldimethylammonium chloride;

alone or as mixtures, or the corresponding salts thereof, and also the macromonomers derived from such monomers.

Preferably, the amphiphilic block polymers have a weight-average molar mass of less than or equal to 100,000 g/mol, more particularly between 1,000 and 50,000 g/mol and preferably between 1,000 and 20,000 g/mol. It is pointed out that the weight-average molar masses indicated above are theoretical molar masses, evaluated as a function of the respective amount of monomers introduced during the preparation of said polymers.

Preferably, an amphiphilic block polymer of nonionic type is used.

As examples of amphiphilic block polymers that are suitable for carrying out the invention, mention may be made of polyhydroxystearate-polyethylene glycol-polyhydroxystearate triblock polymers (the products of the Arlacel range from ICI are an example thereof), and polyalkyl polyether grafted polydimethyl-siloxane block polymers (for instance the products of the Tegopren brand name sold by Goldschmidt).

According to a second variant, the inverse emulsion comprises at least one cationic surfactant.

In the case of this variant, it is indicated that the cationic surfactant does not satisfy the Bancroft rule mentioned previously. Specifically, the cationic surfactant is soluble in the dispersed phase and not in the continuous phase of the inverse emulsion.

Among the suitable cationic surfactants that may especially be used are aliphatic or aromatic fatty amines, aliphatic fatty amides and quaternary ammonium derivatives (Rhodaquat RP50 from Rhodia Chimie).

Finally, a third variant of the invention consists in combining the two possibilities that have just been detailed.

Irrespective of the variant selected, the total amount of nonionic surfactant, of amphiphilic block polymer and/or of cationic surfactant more particularly represents from 0.1% to 10% by weight and preferably from 2% to 10% by weight relative to the internal aqueous phase.

In accordance with one particularly advantageous embodiment, in the case where the organic phase is in the form of an inverse emulsion, the internal aqueous phase may comprise at least one additive chosen from salts such as alkali metal or alkaline-earth metal halides (for instance sodium chloride or potassium chloride), or alkali metal or alkaline-earth metal sulfates (for instance calcium sulfate), or mixtures thereof. The internal aqueous phase may also comprise, as additive, at least one sugar, for example such as glucose, or at least one polysaccharide, such as, especially, dextran, or mixtures thereof.

The concentration of salt in the internal aqueous phase, when a salt is present, is more particularly between 0.05 and 1 mol/l and preferably 0.1 to 0.4 mol/l.

The concentration of sugar and/or polysaccharide is such that the osmotic pressure of the internal aqueous phase comprising said sugar and/or polysaccharide corresponds to the osmotic pressure of an internal aqueous phase comprising 0.05 to 1 mol/l of salt.

According to an important characteristic of the invention, the aqueous phase of the emulsion comprises at least one heat-induced thickening polymer.

Heat-induced thickening polymers have the particular feature of giving aqueous solutions whose viscosity increases when the temperature exceeds the thickening temperature of the heat-induced thickening polymer; above this temperature, the viscosity of the medium in which said polymer is present increases.

More particularly, these polymers are soluble in water at room temperature, and above the thickening temperature, some of the polymer becomes hydrophobic (heat-sensitive portion): the polymer thus forms a physical network at the microscopic level, which is reflected at the macroscopic level by an increase in the viscosity.

As has been mentioned previously, the heat-induced thickening polymers used in the process according to the invention are chosen from those with a viscosity jump between 25 and 80° C. such that the value of the $\log_{10}$ (viscosity at 80° C.)/$\log_{10}$ (viscosity at 25° C.) ratio is at least equal to at least 1.

The ratio is measured under the following conditions:
- The polymer is first dissolved in water (solids content of 4%).
- The rheological profile is then measured in controlled-stress flow mode, by performing a temperature sweep between 20° C. and 80° C. The configuration used is the cone/plate 4 cm/1 degree geometry. The stress induced in the program is chosen (in manual mode) such that the gradient at 25° C. is 10 s$^{-1}$.
- The magnitude selected to characterize the heat-induced thickening power of the polymer, i.e. the $\log_{10}$ (viscosity at 80° C.)/$\log_{10}$ (viscosity at 25° C.) ratio, represents the jump in viscosity, expressed in decades, from 25 to 80° C. In other words, this magnitude indicates that the viscosity of the medium at 80° C. is $10^n$ times greater than the viscosity of the medium at 25° C.; with n being an integer between 0 and 5.

According to one preferred embodiment of the invention, the heat-induced thickening polymer has a jump in viscosity of at least one decade and preferably of at least two decades.

Besides this characteristic, the heat-induced thickening polymers are chosen such that the viscosity variation is reversible. In other words, the viscosity decreases when the temperature decreases.

Among the heat-induced thickening polymers that may be used, mention may be made of hydrophobic modified polysaccharides, for instance carboxymethyl celluloses, methyl celluloses, hydroxyethyl celluloses and hydroxypropyl celluloses.

In the case of polymers of this type, it may be advantageous to use them in combination with at least one additional surfactant chosen from nonionic and anionic surfactants.

Synthetic polymers, for instance polymers based on N-isopropylacrylamide and polymers based on N,N-dimethylaminoethyl methacrylate, are also suitable for use.

According to one particular embodiment of the invention, the heat-induced thickening polymers used have a comb structure consisting of a polymer skeleton segment onto which are grafted at least two identical or different polymeric side segments, for which either the polymer skeleton or the polymeric side segments have a lower critical solution temperature, LCST, of between 25 and 80° C.

It should be noted that the term "segments" covers either a linear chain or a branched chain.

According to a first variant of the invention, it is the polymeric skeleton segment that has an LCST of between 25 and 80° C.

According to a second variant of the invention, which is preferred, it is the polymeric side segments that have an LCST of between 25 and 80° C.

Finally, according to another variant of the invention, several polymers are used, which are arranged together so as to form a crosslinked structure in which the polymer segments thereof having the LCST contain the crosslinking nodes and at least some of the segments thereof not having a lower critical solution temperature of between 25 and 80° C. establish connections between said nodes.

According to these variants, the segment not having the required LCST, i.e. of between 25 and 80° C., is itself water-soluble at least in this temperature range, preferably between 10 and 100° C.

As regards the polymer segment not having an LCST critical temperature, it is more preferably a polymer of water-soluble ethylenic type.

These water-soluble polymers may be derived from the polymerization of water-soluble ethylenic monomers. These monomers may in particular be of vinyl, acrylic, styrene or diene type or alternatively of vinyl ester type.

Examples of vinyl monomers that may be mentioned include vinylsulfonic acid and methallyl-sulfonic acid, or salts thereof.

Examples of acrylic monomers that may be mentioned include (meth)acrylic acid, diacids such as fumaric acid and itaconic acid, or salts thereof, maleic anhydride, acrylamide and its derivatives such as acrylamidomethylpropanesulfonic acid, or salts thereof.

Examples of styrene monomers that may be mentioned include styrenesulfonic acid and vinylbenzoic acid, or salts thereof.

The water-soluble monomers mentioned above may also be combined or substituted with hydrophobic monomers, the units of which, once incorporated into the polymer chain, may be converted, especially by means of a chemical treatment such as hydrolysis, into water-soluble units. Examples of these include methyl (meth)acrylate, tert-butyl (meth)acrylate, glycidyl (meth)acrylate and vinyl acetate.

Finally, organosoluble monomers of any type may also be used and incorporated into the polymer chain in the form of hydrophobic units. Said monomers, which are present in small amounts in the polymer segment, allow the water solubility of the corresponding polymer to be controlled.

Needless to say, the various monomers are selected such that the corresponding polymer segment has a solubility in aqueous medium in accordance with the invention. This adjustment of the relative amounts of corresponding monomers is within the capability of a person skilled in the art.

Monomers such as acrylic acid or methacrylic acid, acrylamides and derivatives thereof, fumaric acid and maleic acid, and sulfonated monomers such as 2-acrylamidomethylpropanesulfonic acid and its alkaline salts, and vinyl sulfonate, are especially preferred according to the invention.

More preferably, this type of polymer segment has a molecular weight at least greater than 1,000 g/mol and preferably at least greater than 20,000 g/mol (measured by aqueous GPC, calibration: PEO).

These polymer segments are advantageously derived from the polymerization of acrylic acid and/or 2-acrylamidomethylpropanesulfonic acid.

As regards the polymer segments with an LCST of between 25 and 80° C., they are derived from polyoxyalkylene polymers.

According to one preferred embodiment of the invention, the various oxyalkylene units present in the polyoxyalkylene polymer contain not more than 6 carbon atoms.

Preferably, the segments with an LCST consist of oxyethylene (OE) units and/or oxypropylene (OP) units.

The OE and OP units may be arranged in the polymeric heat-sensitive segment in random, block or sequential form. The polymeric heat-sensitive segment may have, for example, a starburst structure. It is found to be possible to adjust the critical solution temperature especially by means of the length and composition of these polymer segments. Preferably, the segments with a critical temperature in accordance with the invention consist of at least 5 oxyalkylene units.

More preferably, they are corresponding macromonomers.

For the purposes of the present invention, a macromonomer denotes a macromolecule bearing one or more free-radical-polymerizable ethylenic functions.

The grafting of the polymeric side segments onto a polymeric skeleton segment may be performed according to standard techniques that are familiar to those skilled in the art (for example European Polymer Journal 4, 343 (1968)).

Among these standard techniques, mention may be made especially of the "direct grafting" and copolymerization techniques.

Direct grafting consists in polymerizing the chosen monomer(s) via a free-radical route, in the presence of the selected monomer to form the skeleton of the final product. If the monomer/skeleton couple and the operating conditions are carefully chosen, there may then be a transfer reaction between the growing macroradical and the skeleton. This reaction generates a radical on the skeleton and it is from this radical that the graft grows. The primary radical derived from the initiator may also contribute to the transfer reactions.

As regards copolymerization, this involves in a first stage the grafting, onto the end of the heat-sensitive segment, of a free-radical-polymerizable function. This grafting may be performed by usual methods of organic chemistry. Next, in a second stage, the macromonomer thus obtained is polymerized with the chosen monomer to form the skeleton, and a "comb" polymer is obtained. It is clear to a person skilled in the art that when polymerization is performed between a macromonomer and a monomer chosen such that these two species combine together strongly by hydrogen bonding, then there is simultaneous direct grafting onto the polymer segment of the macromonomer and incorporation of this macromonomer into the polymer chain by simple polymerization of its polymerizable end. In this case, the structure obtained is substantially more branched or even crosslinked than in the previous two cases.

Preferably, the polymer comprises 0.1 mol % to 50 mol % and preferably 0.1 mol % to 5.0 mol % of polymer segments with an LCST of between 25 and 80° C.

The heat-induced thickening polymers that are most particularly suitable for the invention comprise at least:

polymer prepared from PEO-PPO-PEO triblocks and from acrylic acid (respective molar percentages: 2.3%, 97.7%), preferably by direct grafting, polymer prepared from PEO-PPO-PEO triblock macromonomer and from acrylic acid (respective molar percentages: 1.6%, 98.4%), preferably by copolymerization, polymer prepared from PEO-PPO-PEO triblock macromonomer and from acrylic acid (respective molar percentages: 3%, 97%), preferably by copolymerization, and/or polymer prepared from PEO-PPO-PEO triblock macromonomer and from acrylic acid (respective molar percentages: 2%, 98%), preferably by copolymerization.

These polymers have been described especially in French patent application FR 2 780 422.

The content of heat-induced thickening polymer in the aqueous phase is such that the viscosity of the aqueous phase is from 0.2 to 5 times that of the organic phase and preferably from 0.5 to 2 times that of the organic phase at the preparation temperature of the emulsion; this preparation temperature being greater than or equal to the thickening temperature of the heat-induced thickening polymer.

For indicative purposes, the content of heat-induced thickening polymer is more particularly between 0.5% and 5% by weight relative to the aqueous phase. Preferably, the content of heat-induced thickening polymer is between 1% and 3% by weight relative to the aqueous phase.

The aqueous phase also advantageously comprises:

at least one nonionic surfactant and/or at least one nonionic amphiphilic polymer optionally combined with at least one anionic surfactant and/or at least one anionic amphiphilic polymer; the total content of nonionic and anionic surfactant(s)/amphiphilic polymer(s) is between 0.5% and 10% by weight and preferably between 1% and 5% by weight relative to the organic phase or to the inverse emulsion, if present; the amount of anionic surfactant and/or anionic amphiphilic polymer represents 0.5% to 5% by weight and preferably 0.5% to 2% by weight relative to the weight of nonionic surfactant/nonionic amphiphilic polymer; or at least one anionic amphiphilic polymer optionally combined with at least one anionic surfactant; the total content of anionic amphiphilic polymer/anionic surfactant is between 0.5% and 10% by weight and preferably between 1% and 5% by weight relative to the organic phase or to the inverse emulsion, if present.

As regards the nonionic surfactants, polyalkoxylated nonionic surfactants are preferably used.

Advantageously, said nonionic surfactant is chosen from the following surfactants, alone or as a mixture:

alkoxylated fatty alcohols
alkoxylated triglycerides
alkoxylated fatty acids
alkoxylated sorbitan esters
alkoxylated fatty amines
alkoxylated di(1-phenylethyl)phenols
alkoxylated tri(1-phenylethyl)phenols
alkoxylated alkylphenols the number of alkoxylated, more particularly ethoxylated and/or propoxylated, units is such that the HLB value is greater than or equal to 10.

As regards the polyalkoxylated nonionic amphiphilic polymer, this polymer satisfies the Bancroft rule and the two conditions thereof stated previously, and comprises at least two blocks, one of them being hydrophilic and the other hydrophobic; at least one of the blocks comprising polyalkoxylated units, more particularly polyethoxylated and/or polypropoxylated units.

Everything that has been stated hereinabove in the context of the description of the nonionic hydrophilic monomers and the hydrophobic monomers that may be used to prepare the amphiphilic block polymers forming part of the composition of the inverse emulsion remains valid and will not be repeated here.

For purely indicative purposes, said polymers are obtained by carrying out ring-opening polymerizations, especially anionic polymerizations.

More particularly, said nonionic polyalkoxylated amphiphilic polymers are chosen from polymers whose weight-average molar mass is less than or equal to 100,000 g/mol (measured by GPC, polyethylene glycol standard), preferably between 1,000 and 50,000 g/mol and preferentially between 1,000 and 20,000 g/mol.

Examples of polymers of this type that may be mentioned inter alia include polyethylene glycol/polypropylene glycol/polyethylene glycol triblock polymers. Such polymers are well known and are especially sold under the brand names Pluronic (sold by BASF) and Arlatone (sold by ICI).

According to another embodiment, the nonionic amphiphilic polymer is an amphiphilic block polymer obtained by polymerization of at least one nonionic hydrophilic monomer and of at least one hydrophobic monomer, the proportion and nature of said monomers being such that the resulting polymer satisfies the conditions stated previously (Bancroft rule—two conditions).

These amphiphilic polymers furthermore comprise at least one hydrophobic block and at least one neutral (nonionic) hydrophilic block.

In the case where said polymer comprises at least three blocks, and more particularly three blocks, the polymer is advantageously linear. In addition, the hydrophilic blocks are more particularly located at the ends.

In the case where the polymers comprise more than three blocks, these polymers are preferably in the form of grafted or comb polymers.

The list of the nonionic hydrophilic monomers and the nonionic hydrophobic monomers, and also the various preparation methods, cited in the context of the description of the amphiphilic block polymers, may be repeated in the case of the polymers according to this variant.

However, the preferred hydrophilic monomers are acrylamide and methacrylamide, alone or as a mixture, or in the form of macromonomers; the preferred monomers are the esters of acrylic acid with linear or branched $C_1$-$C_4$ alcohols, such as methyl, ethyl, propyl or butyl acrylate, vinyl esters, for instance vinyl acetate, styrene and α-methylstyrene.

Among the suitable anionic surfactants that may be mentioned, inter alia, alone or as mixtures, are:

alkylester sulfonates, for example of formula R—CH(SO$_3$M)—COOR', in which R represents a $C_8$-$C_{20}$ and preferably $C_{10}$-$C_{16}$ alkyl radical, R' represents a $C_1$-$C_6$ and preferably $C_1$-$C_3$ alkyl radical and M represents an alkali metal cation (sodium, potassium or lithium), substituted or unsubstituted ammonium (methylammonium, dimethylammonium, trimethyl-ammonium, tetramethylammonium, dimethylpiperidinium, etc.) or an alkanolamine derivative (monoethanol-amine, diethanolamine, triethanolamine, etc.).

Mention may be made most particularly of methyl ester sulfonates in which the radical R is $C_{14}$-$C_{16}$; alkylbenzenesulfonates, more particularly of $C_9$-$C_{20}$, primary or secondary alkylsulfonates, especially of $C_8$-$C_{22}$, alkylglycerol sulfonates, sulfonated polycarboxylic acids, such as, for example, those described in GB 1 082 179, and paraffin sulfonates;

- alkyl sulfates, for example of formula $ROSO_3M$, in which R represents a $C_{10}$-$C_{24}$ and preferably $C_{12}$-$C_{20}$ alkyl or hydroxyalkyl radical; M representing a hydrogen atom or a cation of the same definition as above, and also the polyalkoxylated (ethoxylated (EO) or propoxylated (PO), or combinations thereof) derivatives thereof, such as, for example, sodium dodecyl sulfate;
- alkyl ether sulfates, for example of formula $RO(CH_2CH_2O)_nSO_3M$ in which R represents a $C_{10}$-$C_{24}$ and preferably $C_{12}$-$C_{20}$ alkyl or hydroxyalkyl radical; M representing a hydrogen atom or a cation of the same definition as above, n generally ranging from 1 to 4, and also the polyalkoxylated (ethoxylated (EO) or propoxylated (PO), or combinations thereof) derivatives thereof, such as, for example, lauryl ether sulfate with n=2;
- alkylamide sulfates, for example of formula $RCONHR'OSO_3M$ in which R represents a $C_2$-$C_{22}$ and preferably $C_6$-$C_{20}$ alkyl radical, R' represents a $C_2$-$C_3$ alkyl radical, M representing a hydrogen atom or a cation of the same definition as above, and also the polyalkoxylated (ethoxylated (EO) or propoxylated (PO), or combinations thereof) derivatives thereof;
- salts of saturated or unsaturated fatty acids such as, for example, those of $C_8$-$C_{24}$ and preferably of $C_{14}$-$C_{20}$, N-acyl N-alkyltaurates, alkylisethionates, alkylsuccinamates, alkylsulfosuccinates, sulfosuccinate monoesters or diesters, N-acyl sarcosinates and polyethoxycarboxylates; and
- alkyl ester and/or alkyl ether and/or alkylaryl ether phosphates.

Among the anionic polymers that may be used, mention may be made most particularly of block polymers, preferably diblock or triblock polymers, obtained by polymerization of at least one anionic hydrophilic monomer, optionally of at least one nonionic hydrophilic monomer, and of at least one hydrophobic monomer.

In this case also, the choice of monomers and the respective proportions thereof are such that the resulting polymer satisfies the two conditions stated previously (Bancroft rule).

The nonionic and anionic hydrophilic monomers and the hydrophobic monomers, and also the synthetic modes mentioned in the context of the description of the amphiphilic polymers forming part of the composition of emulsions for which the continuous phase is an oil phase, may be used to obtain the polymers according to this variant. Reference may thus be made thereto.

According to one particular embodiment, and still in the case of the variant according to which the organic phase is in the form of an inverse emulsion, it may be advantageous to add to the aqueous phase at least one additive chosen from salts such as alkali metal or alkaline-earth metal halides (for instance sodium chloride or calcium chloride), at least one alkali metal or alkaline-earth metal sulfate (for instance calcium sulfate), at least one sugar (for example glucose) or at least one polysaccharide (especially dextran), or mixtures thereof.

The addition of this type of additive makes it possible to equilibrate, if necessary, the osmotic pressures of the aqueous phase of the emulsion and of the internal aqueous phase (of the inverse emulsion); the salt, sugar and/or polysaccharide concentrations are set in this respect.

Furthermore, depending on the application for which the emulsion according to the invention is intended, or depending on the nature of the active material(s) used, it may be desirable to adjust the pH of the external aqueous phase by adding a base (sodium hydroxide or potassium hydroxide) or an acid (hydrochloric acid).

According to one advantageous variant of the present invention, the aqueous phase of the emulsion may comprise at least one thickening polymer. The purpose of this polymer is to avoid creaming and/or sedimentation of the final emulsion.

For illustrative purposes, thickening polymers extracted from plants and optionally modified may be used, such as carrageenans, alginates, carboxy-methyl celluloses, methyl celluloses, hydroxypropyl celluloses or hydroxyethyl celluloses.

Similarly, thickening polymers such as polysaccharides of animal, plant or bacterial origin may be used; nonlimiting examples that may be mentioned include xanthan gum, guar and derivatives (for example such as hydroxypropyl guar) or polydextroses, or combinations thereof.

When it is present, the content of thickening polymer is more particularly between 0.1% and 2% by weight relative to the aqueous phase and preferably between 0.1% and 0.5% by weight relative to the aqueous phase. It is pointed out that, in this concentration range, the thickening polymer is soluble in the aqueous phase.

The organic phase/aqueous phase weight ratio, or the weight ratio of the internal aqueous phase and organic phase combination/aqueous phase, is usually between 10/90 and 90/10 and preferably between 30/70 and 80/20.

The process for preparing the emulsion more particularly consists in mixing together with stirring:

- the organic phase comprising:
  - optionally at least one hydrophobic active material,
  - optionally the dispersed internal aqueous phase optionally comprising at least one hydrophilic active material and optionally at least one additive; the combination of internal aqueous phase and organic phase comprising at least one nonionic surfactant and/or at least one amphiphilic block polymer, and/or at least one cationic surfactant; and
- the aqueous phase comprising:
  - optionally at least one hydrophilic active material,
  - at least one polyalkoxylated nonionic surfactant and/or at least one nonionic amphiphilic polymer and/or at least one anionic surfactant and/or at least one anionic amphiphilic polymer,
  - at least one heat-induced thickening polymer,
  - optionally at least one additive and optionally at least one thickening polymer;
- the emulsion preparation temperature being greater than or equal to the thickening temperature of the heat-induced thickening polymer.

It is similarly pointed out that the emulsion preparation temperature is preferably greater than or equal to the melting point of the organic phase.

Advantageously, the apparatus used for the stirring is entirely standard in the field. Thus, a frame paddle may be used.

It should be noted that the stirring is relatively slow, of the order of 300 to 700 rpm.

In the case where the organic phase consists of an inverse emulsion, the process consists in first preparing the inverse emulsion and then mixing this emulsion with the aqueous phase.

The preparations of a simple direct emulsion (oil-in-water emulsion) or of a multiple emulsion may themselves also be performed according to any known method.

Thus, by way of example of preparation of a simple direct emulsion, a first mixture comprising the compound constituting the internal organic phase and optionally the hydrophobic active material is first prepared.

Secondly, a second mixture comprising the water, the nonionic and/or anionic surfactant and/or amphiphilic polymer, the heat-induced thickening polymer, optionally the active material and/or the additive (salt, sugar and/or polysaccharide) and/or the thickening polymer is prepared. According to one particular embodiment for preparing a simple direct emulsion, the aqueous phase does not comprise additive or thickening polymer.

The preparation of the aqueous phase preferably consists in first mixing together the water and the active material, if used, followed by the surfactant and/or the amphiphilic polymer, with stirring. Next, the heat-induced thickening polymer is added.

This operation generally takes place at a temperature of between 25 and 80° C. and preferably between 40 and 70° C. It is not necessary for the temperature during the mixing of the various compounds of the aqueous phase to be greater than or equal to the thickening temperature of the heat-induced thickening polymer.

The emulsion is then obtained by adding the organic phase to the aqueous phase, with stirring. It is again pointed out that, according to one characteristic of the invention, this operation takes place at a temperature greater than or equal to the thickening temperature of the heat-induced thickening polymer, so as to limit the difference in viscosity between the two phases of the emulsion.

More particularly, this operation is performed at a temperature of at least 25° C., more particularly between 25 and 80° C. and preferably between 40 and 70° C.

It is possible to carry out a step of refining of the direct emulsion.

The stirring time may be determined without difficulty by a person skilled in the art and depends on the type of apparatus used. It is preferably sufficient to obtain a mean droplet size (d50) that is within the ranges mentioned previously.

In the case of a multiple emulsion, one preparation example consists in preparing a first mixture constituting the internal aqueous phase, comprising the water, optionally the hydrophilic active material, the cationic surfactant, if present, and optionally the additive (salt, sugar and/or polysaccharide). A second mixture is also prepared, comprising the compound constituting the internal organic phase, optionally the hydrophobic active material and the nonionic surfactant and/or nonionic amphiphilic block polymer, if present.

The first mixture is then added to the second mixture, with stirring.

The preparation of the inverse emulsion is generally performed at a temperature greater than the melting point of the compound constituting the internal organic phase. More particularly, the preparation temperature for the inverse emulsion is between 20 and 80° C. Advantageously, the preparation temperature for the inverse emulsion is in the region of the preparation temperature for the multiple emulsion.

It is possible to perform a refining step on the inverse emulsion.

The stirring time may be determined without difficulty by a person skilled in the art and depends on the type of apparatus used. It is preferably sufficient to obtain a mean droplet size (d50) that is within the ranges mentioned previously.

The external aqueous phase of the emulsion is then prepared. This may especially be performed by mixing together the nonionic and/or anionic surfactant and/or amphiphilic polymer, the heat-induced thickening polymer, optionally the active material and/or the additive and/or the thickening polymer and the water. Preferably, the water and the active material, the additive, if present, the surfactant and/or the amphiphilic polymer are first mixed together, with stirring. Next, the heat-induced thickening polymer and, where appropriate, the thickening polymer are added. It is pointed out that, according to one entirely advantageous embodiment, the thickening polymer, if used, is added only once the multiple emulsion has been obtained. In this case, it is used in the form of an aqueous solution. The water content is such that the concentration ranges of the multiple emulsion are satisfied.

This operation generally takes place at a temperature of between 25 and 80° C. and preferably between 40 and 70° C. It is not necessary for the temperature during the mixing of the various compounds of the external aqueous phase to be greater than or equal to the thickening temperature of the heat-induced thickening polymer.

The actual preparation of the multiple emulsion is then performed by adding the inverse emulsion to the aqueous phase, which were prepared previously.

This operation takes place at a temperature greater than or equal to the thickening temperature of the heat-induced thickening polymer.

This operation thus preferably takes place at a temperature of at least 25° C., more particularly between 25 and 80° C. and preferably between 40 and 70° C.

Once the multiple emulsion is obtained, the mixture may be left to cool to a temperature below the thickening temperature of the heat-induced thickening polymer.

The stirring conditions are preferably of the same type as those used during the preparation of the inverse emulsion.

It is pointed out that it would not constitute a departure from the context of the present invention to mix together several multiple emulsions, provided that the external aqueous phases of the mixed emulsions are compatible.

The emulsion according to the invention may be used as a constituent component in formulations that may be used in many fields, such as cosmetics, food, the field of plant-protection active materials, that of oil or gas well exploitation or construction, that of silicones, or alternatively in the field of papermaking, inter alia.

A concrete but nonlimiting example of the invention will now be presented.

EXAMPLE

1. Preparation of the Heat-Induced Thickening Polymer 1.1 Synthesis of the Heat-Sensitive Macromonomer The macromonomer is synthesized in bulk, without catalyst, in the following manner:

Antarox E400 (EO/PO/EO triblock polymer sold by Rhodia Chimie, 200 g) and maleic anhydride (6.74 g) are introduced at room temperature into a 500 ml two-necked glass reactor equipped with a condenser and a magnetic bar.

The temperature is then brought to 60° C. (over about 1 hour), with stirring and flushing with nitrogen, and then to 140° C. (over about 7 hours) and is maintained at this temperature for 18 hours.

The macromonomer obtained is then dissolved in water and neutralized by adding 5M sodium hydroxide.

Its solids content is 28.9% (determined with 1 g of macromonomer solution dried in an oven at 105° C. for 1 hour). The pH is 7.

1.2 Synthesis of the Heat-Induced Thickening Polymer

The heat-induced thickening polymer is synthesized via a free-radical route in aqueous solution using acrylic acid and macromonomer obtained above.

The polymerization is performed at about 45° C.

The redox couple used is ammonium persulfate (oxidizing agent) and ascorbic acid (reducing agent).

The proportions of the various reagents are as follows:

acrylic acid/macromonomer molar ratio: 98/2 ammonium persulfate: 0.18 mol % relative to the acrylic acid ascorbic acid: 0.09 mol % relative to the acrylic acid.

The mass concentration of reagents is in the region of 16%.

The process is as follows:

The ingredients below are introduced into a thermostatically maintained jacketed glass SVL reactor (1.5 l), on which is mounted a tubular condenser, and which is equipped with a mechanical stirrer (anchor), several inlets and a nitrogen inlet:

at 25° C.: the macromonomer in aqueous solution (68.21 g) and water (139.6 g); the temperature is then increased to 45° C.

at 45° C.: introduction of sodium persulfate (0.0316 g); this time is noted $t°$.

From $t°$ to $t°+5$ hours: continuous introduction of acrylic acid (21.01 g) dissolved in water (5.14 g) and partially neutralized with 5M sodium hydroxide (4.71 g);

From $t°$ to $t°+8$ hours: continuous introduction of ascorbic acid (0.013 g) dissolved in water (15 g).

The reactor is then cooled.

The polymer obtained has the following characteristics:

Determination of the solids content by gravimetry (conditions 1.1): 16.47%

Determination of the mean molar mass by aqueous GPC:

Conditions:

water+0.5M $LiNO_3$+0.06M $NaN_3$ at 1 ml/min

3 Shodex SB 806 M columns detector: differential refractometer

This GPC is calibrated with PEO standards; the molar masses obtained are thus relative values. The mass-average molar mass is 310,000 g/mol.

Heat-induced thickening power by rheology:

The viscosity of aqueous solutions containing the heat-induced thickening polymer is measured as a function of the temperature.

The measuring conditions are as follows:

pH=8, polymer solids content of 4%.

The jump in viscosity is measured in controlled-stress flow mode by performing a temperature sweep between 20° C. and 80° C. The configuration used is the cone/plate 4 cm/1 degree geometry. The stress induced in the program is chosen (in manual mode) such that the gradient at 25° C. is 10 $s^{-1}$.

The jump in viscosity between 25 and 80° C., corresponding to the ratio $\log_{10}$ (viscosity at 80° C.)/$\log_{10}$ (viscosity at 25° C.), expressed in decades, is 3.

2. Preparation of an Emulsion 2.1 Preparation of an Inverse Emulsion 68.6 g of Napvis D30 polybutene (sold by BP) and 1.6 g of Tegopren 7006 (polyalkyl polyether grafted polydimethylsiloxane, sold by Goldschmidt) are successively introduced into a 250 ml beaker.

The mixture is homogenized by stirring with a frame paddle at 250 rpm for 10 minutes, the organic phase being placed in a water bath thermostatically maintained at 70° C.

The aqueous phase is then introduced dropwise under the same stirring conditions.

The amount of aqueous phase is such that the aqueous phase/organic phase weight ratio is 30/70.

The aqueous phase comprises 5.2 g of lactic acid (0.1M), 26.2 g of sodium chloride (0.1M) and 0.18 g of Phenonip (biocide, sold by NIPA Laboratories).

Once the aqueous phase has been introduced, the emulsion is refined by stirring with the frame paddle for 10 minutes at 400 rpm, and then for 15 minutes at 600 rpm.

2.2 Preparation of the Multiple Emulsion

The external aqueous phase is prepared as follows:

5 g of the heat-induced thickening polymer solution obtained in point 1.2, 20 g of Arlatone F127G at 5% ((EO)x(PO)y(EO)z polymer with verification of the following equation: 82<x+z<90 and 7 PO units per mole of polymer, sold by ICI) and 20 g of distilled water are mixed together.

The initial pH is adjusted by adding sodium hydroxide (2M) to reach a pH of 6-7 (measured at 23° C.).

The resulting external aqueous phase is introduced into a water bath at 50° C. with stirring using a TT paddle at 250 rpm, until a homogeneous phase is obtained.

0.5 g of Phenonip is then added.

46.8 g of the inverse emulsion obtained previously are introduced by cumulative successive additions to the external aqueous phase, at 50° C., with stirring at 500 rpm for 10 minutes for each addition.

Once the introduction of the inverse emulsion is complete, a refining operation is performed using a TT paddle at 700 rpm for 30 minutes.

The internal aqueous phase/organic phase/external aqueous phase weight proportion is 16/35/49.

The mean droplet size is between 5 and 10 μm (Horiba).

The invention claimed is:

1. A process for the preparation of an oil-in-water emulsion whose organic phase has a viscosity of greater than or equal to 1 Pa.s at 25° C., comprising the step of mixing together with stirring:

the organic phase, and an aqueous phase comprising at least one heat-induced thickening polymer displaying a thickening temperature and a jump in viscosity between 25 and 80° C. such that:

said jump in viscosity has a ratio $\log_{10}$ (viscosity at 80° C.)/$\log_{10}$ (viscosity at 25° C.) of at least equal to 1, and said jump in viscosity has a variation in viscosity being reversible; the amount of heat-induced thickening polymer being such that the aqueous phase has a viscosity of from 0.2 to 5 times that of the organic phase, said emulsion being prepared at a preparation temperature greater than or equal to the thickening temperature of the heat-induced thickening polymer.

2. The process as claimed in claim 1, wherein the organic phase has a viscosity of at least equal to 2.

3. The process as claimed in claim 1, wherein the heat-induced thickening polymer presents a comb structure, consisting of a polymer skeleton onto which are grafted at least two identical or different polymeric side segments, and wherein either the polymer skeleton or the side segments have a lower critical solution temperature of between 25 and 80° C.

4. The process as claimed in claim 3, wherein the polymeric side segments of the heat-induced thickening polymer have a lower critical solution temperature of between 25 and 80° C.

5. The process as claimed in claim 4, wherein the segments not having a lower critical solution temperature of between 25 and 80° C., are water-soluble at least in this temperature range.

6. The process as claimed in claim 4, wherein the polymer segments not having a lower critical solution temperature, are water-soluble in the temperature range for preparation of the emulsion.

7. The process as claimed in claim 4, wherein the polymer segments not having a lower critical solution temperature are water-soluble ethylenic polymers.

8. The process as claimed in claim 7, wherein the water-soluble ethylenic polymers are prepared from the polymerization of water-soluble ethylenic monomers of vinyl, acrylic, styrene, or vinyl ester type monomers.

9. The process as claimed in claim 3, wherein the polymer side segments having a lower critical solution temperature of between 25 and 0° C. are polyalkoxylated polymers.

10. The process as claimed in claim 9, wherein the polymer side segments contain at least 5 oxyalkylenated units.

11. The process as claimed in claim 1, wherein the heat-induced thickening polymer is used in an amount such that the viscosity of the aqueous phase is from 0.5 to 2 times that of the organic phase, at the preparation temperature of said emulsion.

12. The process as claimed in claim 1, wherein the heat-induced thickening polymer is present in a content of between 0.5% and 5% by weight of the aqueous phase.

13. The process as claimed in claim 1, wherein the organic phase has a viscosity of at least 5 Pa.s.

14. The process as claimed in claim 1, wherein the organic phase are mineral oils, alkyd resins, polyisocyanates or high molecular weight silicones.

15. The process as claimed in claim 1, wherein the organic phase further comprises at least one hydrophobic active material.

16. The process as claimed in claim 1, wherein the organic phase comprises a dispersed internal aqueous phase.

17. The process as claimed in claim 16, wherein the internal aqueous phase comprises at least one hydrophilic active material.

18. The process as claimed in claim 16, wherein the organic phase presents an internal aqueous phase/organic phase weight ratio of between 10/90 and 90/10.

19. The process as claimed in claim 1, wherein the emulsion presents a organic phase/aqueous phase weight ratio, of between 10/90 and 90/10.

20. The process as claimed in claim 16, wherein the emulsion presents a weight ratio of the internal aqueous phase and organic phase combination/aqueous phase, of between 10/90 and 90/10.

21. The process for the preparation of an oil-in-water emulsion whose organic phase has a viscosity of greater than or equal to 1 Pa.s at 25° C., comprising the step of mixing together with stirring:

the organic phase, and an aqueous phase comprising at least one heat-induced thickening polymer displaying a thickening temperature and a jump in viscosity between 25 and 80° C. such that:

said jump in viscosity has a ratio $\log_{10}$ (viscosity at 80° C.)/$\log_{10}$ (viscosity at 25° C.) of at least equal to 1, and said jump in viscosity has a variation in viscosity being reversible; the amount of heat-induced thickening polymer being such that the aqueous phase has a viscosity of from 0.2 to 5 times that of the organic phase, said emulsion being prepared at a preparation temperature greater than or equal to the thickening temperature of the heat-induced thickening polymer, and the emulsion obtained being then cooled to a temperature below the thickening temperature of the heat-induced thickening polymer.

* * * * *